United States Patent [19]
Dickie

[11] Patent Number: 5,231,973
[45] Date of Patent: Aug. 3, 1993

[54] VAGINAL SPECULUM

[75] Inventor: Robert G. Dickie, Newmarket, Canada

[73] Assignee: Advanced Medical Devices Incorporated, Toronto, Canada

[21] Appl. No.: 454,559

[22] Filed: Dec. 21, 1989

[51] Int. Cl.⁵ ............................................. A61B 1/32
[52] U.S. Cl. ................................................... 128/17
[58] Field of Search ....................... 128/17, 18, 20; 606/197, 198

[56] References Cited

U.S. PATENT DOCUMENTS

| | | | |
|---|---|---|---|
| 3,246,646 | 4/1966 | Murphy | 128/17 |
| 3,332,414 | 7/1967 | Gasper | 128/17 |
| 3,575,163 | 4/1971 | Gasper | 128/17 |
| 3,716,047 | 2/1973 | Moore et al. | 128/18 |
| 3,890,961 | 6/1975 | Moore et al. | 128/17 |
| 3,985,125 | 10/1976 | Rose | 128/17 |
| 4,385,626 | 5/1983 | Danz | 128/17 |
| 4,766,887 | 8/1988 | Cecil | 128/17 |

FOREIGN PATENT DOCUMENTS 157473  2/1883  France ................................. 128/17

OTHER PUBLICATIONS

Codman & Schurtleff, Inc., A to Z Catalog for Surgical Products, pp. 536-537, Dec. 1987.

*Primary Examiner*—Mark S. Graham
*Attorney, Agent, or Firm*—Robert O. Nimtz

[57] ABSTRACT

A vaginal speculum is disclosed in which a ratcheted linear motion of a thumb pad is translated into a complicated linear, rotational and retractive motion of the speculum paddles to provide anatomically correct motions for dilation of the vagina and the cervix without complicated two-handed adjustments of the speculum. Cam follower pins follow the contours of a cam slot to translate the linear motion into the required complicated motions of the speculum paddles. The ratchet permits easy locking at any degree of opening while unlocking is accomplished simply by depressing the thumb pad to disengage the pawl from the ratchet bars. A fluid reservoir is built into the speculum to capture fluids discharged during examination.

11 Claims, 3 Drawing Sheets

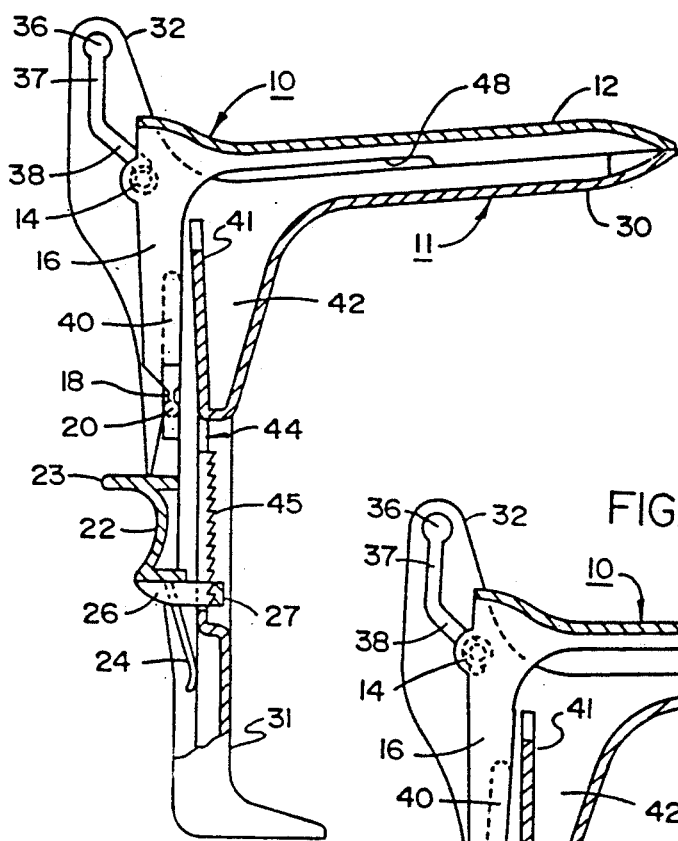
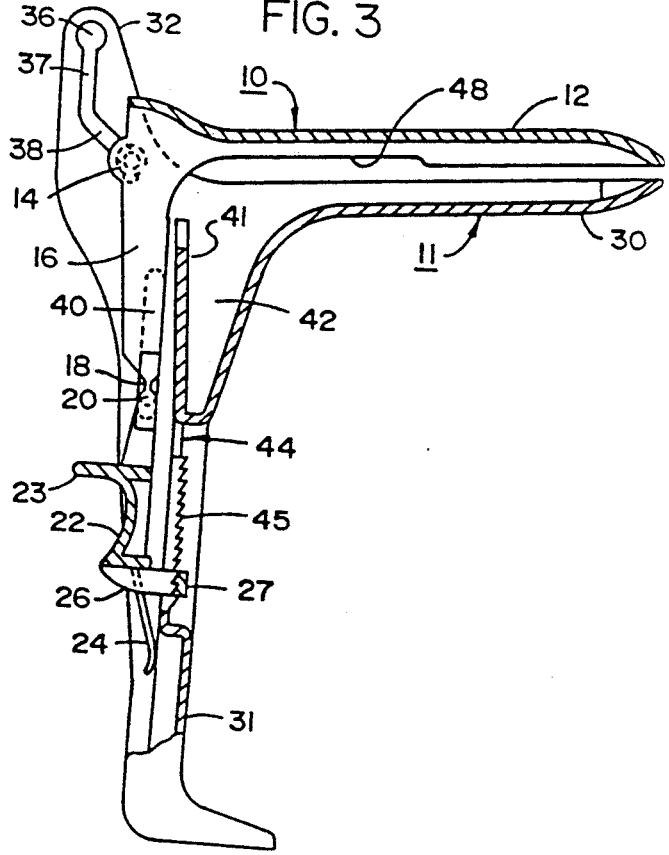

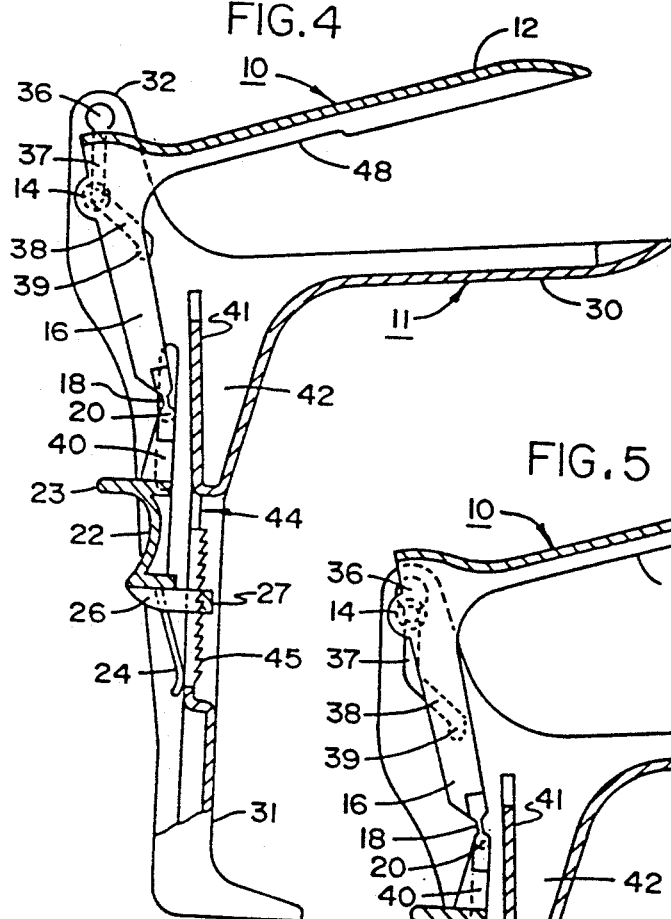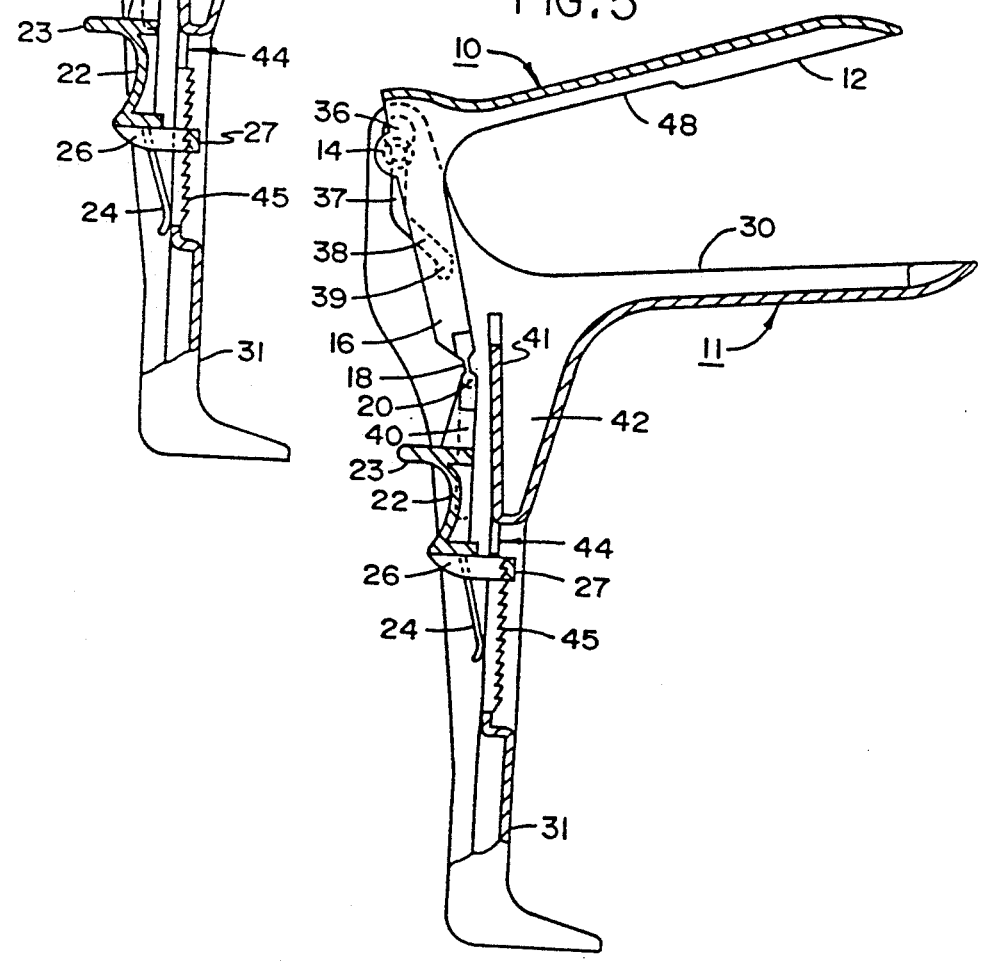

VAGINAL SPECULUM

TECHNICAL FIELD

This invention relates to medical specula and, more particularly to single control point, multiply articulated vaginal specula.

BACKGROUND OF THE INVENTION

In order to facilitate the examination of internal body cavities with an external orifice, it is sometimes necessary to employ an instrument to dilate the orifice and the cavity. Such instruments are called specula. Specula for examination of the cervix employ a pair of paddles or blades which are inserted into the vagina. The paddles are then separated to dilate the vaginal orifice and permit examination of the cervix. Ideally, the articulation of the paddles of a vaginal speculum encompasses three distinct movements. One is a rotational motion around one end of the paddles to provide an angled opening between the paddles which accommodates the internal topology of the cavity. A second motion is the linear separation of the paddles to cause adequate dilation of the cavity for examination. The third motion is a retraction of the upper paddle relative to the lower paddle to avoid scrapping the upper inner surface of the cavity.

In prior art specula, one of which is disclosed in W. P. Murphy Jr., U.S. Pat. No. 3,246,646, granted Apr. 19, 1966, all three of these desirable motions were not always accommodated. More importantly, each of these motions required, in the prior art, separate and independent adjustments by the user, a clumsy procedure which prolongs the examination and often causes discomfort to the examinee. Finally, prior art specula made of inexpensive plastic designed to be thrown away after a limited number of uses, require a substantial number of independently manufactured parts, tend to be flimsy due to the motion adjustment mechanisms, and often broke while in use.

SUMMARY OF THE INVENTION

In accordance with the illustrative embodiment of the present invention, these and other problems are overcome by an improved speculum made of only two parts and including a single adjustment mechanism that simultaneously accommodates three distinct motions of the paddles, i.e., pivotal, linear and retractive. More particularly, the upper paddle is captured in a cam slot in the lower paddle with a preselected cam profile or trajectory. Using a thumb pad, pivotally connected to the upper paddle, to slide the upper paddle relative to the lower paddle causes the cam follower in the upper paddle to move in a path which automatically and simultaneously causes the upper paddle to undergo all of the above-described motions.

In accordance with one feature of the present invention, the thumb operated upper paddle is assembled to a handle on the lower paddle by means of a spring-biased pawl which engages a ratchet bar on the handle to provide continuously ratcheted opening motion but allowing disengagement of the pawl from the ratchet by depressing the thumb pad when the specula is to be collapsed and withdrawn. In the preferred embodiment, a double ended pawl engages two distinct ratchet bars, one on each side of a pawl extension arm, to provide improved and more reliable ratcheting action.

In accordance with another important feature of the present invention, the upper paddle is connected to the thumb pad by arms terminating in a pivot member which allows the upper portion of the paddle to rotate with respect to the lower portion. In metallic specula, this pivot member would be a standard metallic axle and bearing. In accordance with one aspect of the present invention, in plastic specula the thumb pad is connected to the upper paddle by thin strips of plastic forming "living hinges" which allow the upper paddle to rotate with respect to the thumb pad (and the lower paddle attached thereto). Cylindrical pins at one end of the hinges and riding in a linear vertical slot in the handle of the lower paddle confine the motion of the thumb pad end of the upper paddle arms, thus forcing the upper paddle to move in accordance with the cam profile.

In accordance with another feature of the invention, the lower paddle has a built-in fluid reservoir fashioned integrally with the inner surface of the lower paddle to catch any fluids discharged during the course of the examination, thereby avoiding the discharge of such fluids onto the hands of the user on onto the examination table or the floor.

In accordance with yet another feature of the invention, the cam slot profile provides for a small linear closing motion of the upper paddle when collapsing the specula after the examination. This avoids a scissoring motion on closure which can cause pinching of the labial tissues at the cavity opening.

Finally, and in accordance with yet another feature of the invention, the inner edges of the paddles are shaped to leave a small gap between the paddles at the pivoting end, thereby further reducing the possibility of pinching when the specula is collapsed for withdrawl.

A major advantage of the present invention is that the specula user can operate the specula with one hand and yet obtain all of the desired paddle arm motions smoothly and quickly. Moreover, the improved speculum can be manufactured in only two pieces of inexpensive plastic by injection molding techniques. This permits throwing the speculum away after a single use and hence sterilization is not required. The same principles can, of course, be applied to metallic specula with a normal metallic hinge to obtain the smooth, rapid and comfortable thumb-controlled dilation of the body cavity and smooth rapid collapse of the speculum for withdrawal.

BRIEF DESCRIPTION OF THE DRAWINGS

A complete understanding of the present invention may be gained by considering the following detailed description in conjunction with the accompanying drawing, in which:

FIG. 2 is a side cross-sectional view of the assembled speculum of FIG. 1 in the closed position for insertion or withdrawal from the body cavity to be examined, showing the thumb pad in the fully retracted starting position;

FIG. 3 is a side cross-sectional view of the assembled speculum of FIG. 1 in a slightly ajar position, showing the initial linear relative motion of the upper and lower paddles when the thumb pad is in the initial opening or final collapsing stages of movement;

FIG. 4 is a side cross-sectional view of the assembled speculum of FIG. 1 in a half open position, showing the intermediate relative motion of the upper and lower paddles including linear separation, rotation and retraction of the upper paddle while the thumb pad is in intermediate stages of movement; and FIG. 5 is a side cross-sectional view of the assembled speculum of FIG. 1 in a fully open position, showing the linear, non-rotational relative movement of the upper and lower paddles during the final opening stages of movement of the thumb pad.

To facilitate reader understanding, identical reference numerals are used to designate elements common to the figures.

DETAILED DESCRIPTION

Figure 1:
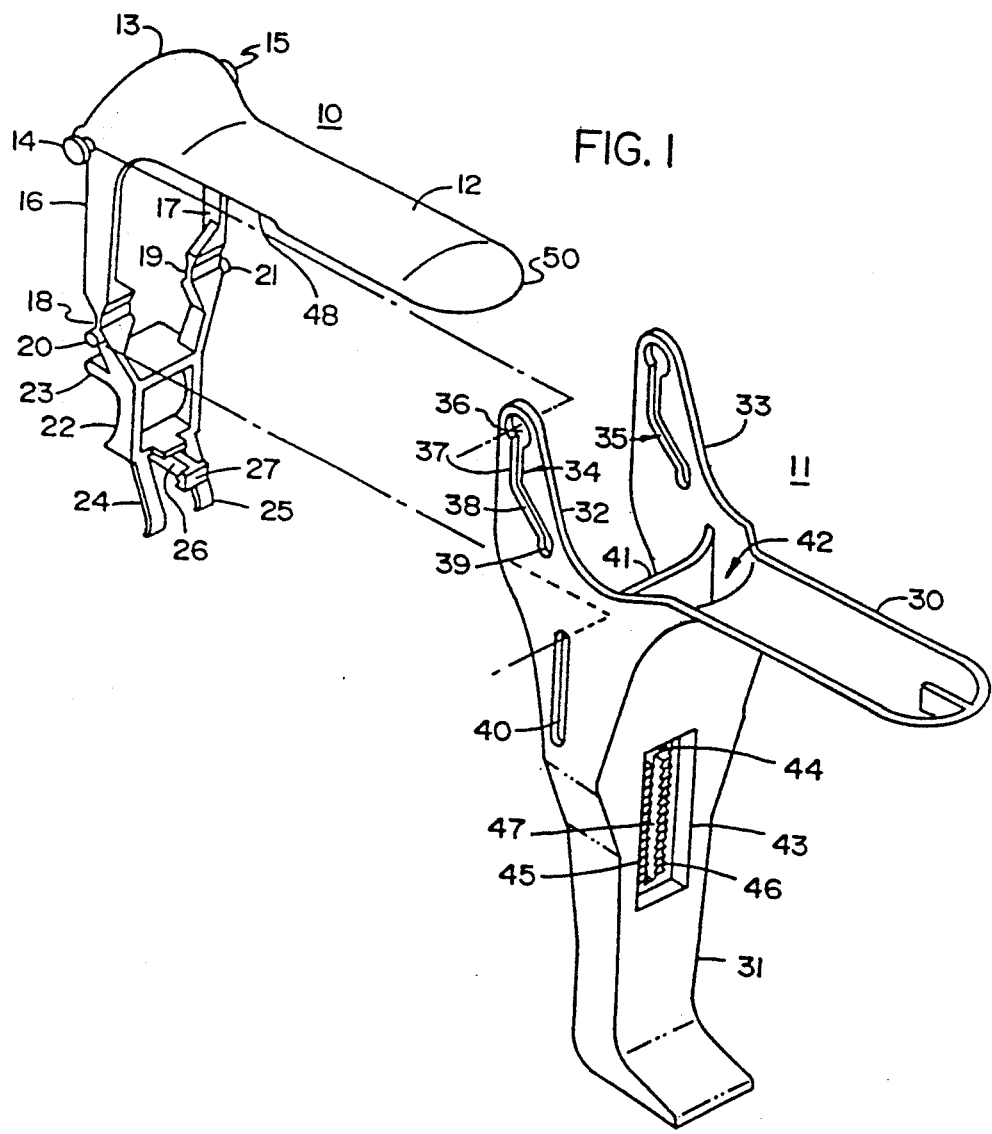
FIG. 1 shows a perspective, exploded view of the two paddle members of a molded plastic single-action speculum in accordance with the present invention.

Referring more particularly to FIG. 1, there is shown a perspective exploded view of a plastic vaginal speculum in accordance with the present invention comprising an upper paddle member 10 and a lower paddle member 11. Upper paddle member 10 comprises a dilator blade or paddle 12 designed to be inserted into the vaginal opening for purposes of examination. Paddle 12 has a rounded nose 50 and an enlarged base 13. At the lateral extremities of the base 13 are cam follower pins 14 and 15, having enlarged heads and smaller diameter follower surfaces. Paddle base 13 is connected to two arms 16 and 17, each terminating in a thin strip 18 and 19, respectively, of plastic material. Strips 18 and 19 comprise "living hinges" which permit rotational motion of paddle 12. That is, the plastic material has sufficient flexibility to bend in the areas of strips 18 and 19. The cross sectional area of strips 18 and 19 can be adjusted to provide any desired degree of elasticity.

Situated below strips 18 and 19 are retention pins 20 and 21, respectively which, in turn, are connected to a thumb pad 22. Thumb pad 22 may be knurled on the rear face to provide adequate thumb friction and includes an overhang 23 against which the thumb may be pushed in order to move the paddle member 10 in an upward direction. Below thumb pad 22 are two molded springs 24 and 25. Connected to thumb pad 22 on the side opposite to the face of thumb pad 22 is a pawl arm 26 to which is attached a double-sided pawl 27. That is, a toothed surface is provided on pawl 27 on either side of pawl arm 26.

Lower paddle member 11 comprises a lower dilator blade or paddle 30 attached to a handle 31 formed with three sides of plastic material. At the upper end of handle 31 are two extensions 32 and 33, each of which includes one of a matching pair of cam slots 34 and 35, respectively. Cam slots 34 and 35 are identical and hence only cam slot 34 will be described in detail. Cam slot 34 has an upper round opening 36 sufficiently large to accommodate the enlarged head of cam follower pin 14. Below opening 36 is a vertical slot portion 37, a slanted slot portion 38 and a short vertical slot portion 39. Below cam slots 34 and 35 are a pair of matching vertical retention slots only one of which, slot 40, is visible in FIG. 1. Pins 20 and 21 fit into the pair of slots corresponding to slot 40 to trap the lower portion of upper paddle member 10 in sliding contact with the rear face of handle 31. A plastic wall 41 between the two side extensions 32 and 33 and in front of slot 40 forms a reservoir 42 capable of holding a small amount of liquid.

In the front face of handle 31 is an elongated vertical recess 43 having a rectangular opening 44 at the top which accommodates pawl 27. At either side of a central slot 47 in recess 43 are a pair of ratchet bars 45 and 46 which can be engaged by the toothed surfaces on pawl 27. Central slot 47 permits pawl arm 26 to slide between ratchet bars 45 and 46.

Upper paddle member 10 is assembled to lower paddle member 11 by inserting pawl 27 through opening 44. Simultaneously, extensions 32 and 33 are spread laterally sufficiently to insert cam followers 14 and 15 into holes corresponding to opening 36 in extensions 32 and 33. At the same time, pins 20 and 21 are inserted into slots in member 11 corresponding to slot 40. Once assembled in this manner, by depressing thumb pad 22, the upper paddle member 10 can be slid down on lower paddle member 11 until pawl 27 reaches the bottom of slot 47, pin 20 reaches the bottom of slot 40 and cam follower pin 14 reaches the bottom of cam slot 39. In this position, the paddles 12 and 30 are closed on each other and the vaginal specula of FIG. 1 is completely assembled for packaging, storage and shipping.

As previously noted, the vaginal speculum of FIG. 1 can be fabricated of metal, preferable stainless steel, and be reused as often as desired by sterilizing between uses. The living hinges 18 and 19 would, of course, be replaced by metallic hinge elements. In the preferred embodiment, however, the entire instrument is made of plastic and is sufficiently inexpensive to be discarded after only one use. One such standard grade sterile plastic is known as CYCOLAC HP-20, manufactured by the General Electric Company. Alternatively, a reusable plastic such as LEXAN ® HPS-1 Transparent, also manufactured by the General Electric Company, can be used and the plastic speculum sterilized in an autoclave between up to ten successive uses.

The operation of the vaginal speculum of FIG. 1 will be described in connection with FIGS. 2 through 5. In FIG. 2 there is shown a cross sectional elevation view of the assembled speculum in its fully closed position. It can be seen in FIG. 2 that the cam follower pin 14 is at the bottom of cam slot 34. Similarly, retention pin 20 is at the bottom of retention slot 40 and pawl 27 is at the bottom of ratchet bar 45. Spring 24 is flexed against the inner surface of handle 31 to lock pawl 27 into locking contact with ratchet bar 45. The vaginal speculum of FIG. 1 therefore remains locked in the closed position shown in FIG. 2 for packaging, storage and shipping. The speculum is also in this closed or collapsed position when the paddles 12 and 30 are inserted into the vaginal opening preliminary to an examination of the cervix.

In FIG. 3 there is shown another cross sectional elevation view of the assembled speculum in a slightly opened position. If the thumb pad 22 is pushed upward, pawl 27 is free to ride upward on the sloped surface of the teeth of ratchet bars 45 and 46. The lower ends of hinges 18 and 19 are constrained to move only vertically due to the retention pins 20 and 21 being trapped in retention slots 40. The upper portion of upper paddle member 10, above hinge 18, is free to pivot on hinge 18 as dictated by the profile or trajectory of cam slot 38. Due to the short vertical section 39 of cam slot 34, the initial movement of upper paddle 12 is a linear vertical displacement away from lower paddle 30 as illustrated in FIG. 3.

In FIG. 4 there is shown yet another cross sectional elevation view of the assembled speculum of FIG. 1 in a half opened position. As can be seen in FIG. 4, as thumb pad 22 is ratcheted further upwards, cam follower pin 14 is forced to slide diagonally backward and upward in ramped portion 38 of cam slot 34. Moving the upper portion of paddle member 10 (above hinge 18) backward forces paddle 12 to rotate with respect to paddle 30 and, at the same time, retract backward with respect to paddle 30. The rotational portion of this motion starts to dilate the vaginal opening and the cervix while the retractive portion of this motion orients upper paddle 12 away from the downwardly curving upper surface at the inner end of the cervix. FIG. 4 depicts the position of the paddles 12 and 30 at the end of this combined rotational and retractive movements.

In FIG. 5 there is shown yet another cross sectional elevation view of the assembled speculum of FIG. 1 in the fully opened position. Again, as thumb pad 22 is ratcheted further upward, cam follower pin 14 slides in the vertical portion 37 of cam slot 34, causing upper paddle 12 to move vertically away from lower paddle 30, but without any further rotational motion. The amount of the rotational opening is, of course, adjusted to accommodate the topology of the typical inner surfaces of a cervix. As can be better seen in FIG. 1, the user of the speculum can now perform the examination by viewing the interior of the cervix between paddles 12 and 30 and between arms 16 and 17.

From the above description, it can be seen that the vaginal speculum of the present invention can be operated entirely by one hand and with a single continuous motion of the thumb pad 22. Specula can, of course, be manufactured with paddles 12 and 30 of varying widths and lengths to accommodate patients of various sizes. The speculum will ratchet upward, locking at every tooth position of ratchet bars 45 and 46. The user therefore merely pushes thumb pad 22 upward until the desired degree of vaginal dilation is accomplished. Due to the ratchet mechanism, the speculum of the present invention will lock in an open position at any degree of opening due to the close small teeth in ratchet bars 45 and 46. Once the examination is complete, the user simply depresses thumb pad 22 to disengage pawl 27 and to allow the thumb pad 22 to move downward, collapsing the paddles 12 and 30 together. The final linear movement of paddles 12 and 30, depicted in FIG. 3, avoids pinching labial tissues at the vaginal opening which sometimes occurs due to the scissoring action of rotational closure. An undercut 48 on the inner surface of upper paddle 12 leaves a small space between paddles 12 and 30 when these paddles are fully closed (FIG. 2), further protecting against pinching of tissues while collapsing the instrument. Once collapsed, the speculum can be withdrawn from the vaginal opening without any discomfort.

Note that the use of a cam slot and a cam follower pin in the cam slot permits precise and detailed control over the movement of the upper paddle 12. A single vertical adjustment by the user is thereby translated into a complicated combination of vertical, rotational and retractive motions, all of which can be separately specified by the design of the cam slot profile. Only one hand is required to operate the speculum. The elasticity of the living hinges 18 and 19 assist in the collapse of the paddles 12 and 30 when thumb pad 22 is depressed.

It will also be noted that the cam follower pin, the cam slot, the retainer pin, the retainer slot, the living hinges, the springs, the pawl and the ratchet bars are all duplicated, one on each lateral side of the speculum. This duplication provides increased reliability since, if any one of these parts is damaged, the matching part on the other side of the speculum will permit continued operation of the speculum. Finally, the ratchet mechanism locks the paddles in any open position desired, with no action required by the user.

If, as often occurs, fluids are discharged during examination, the reservoir 42 catches these fluids to prevent discharge of these fluids onto the user's hands or clothing of the user. This built-in reservoir therefore contributes to the convenience of use of the speculum while, at the same time, improving sanitary conditions during its use.

It should also be clear to those skilled in the art that further embodiments of the present invention may be made by those skilled in the art without departing from the teachings of the present invention.

What is claimed is:

1. A speculum comprising:
   a first L-shaped paddle member having a first dilator paddle at one end and a handle at the other end, said first paddle member having an inner surface and an outer surface,
   a second L-shaped paddle member having a second dilator paddle at one end and an actuator at the other end, said second paddle member also having an inner surface and an outer surface,
   said second L-shaped paddle member having a pivot member connecting said one end of said second paddle member to said other end of said second paddle member to permit said one end of said second paddle member to rotate with respect to said other end of said second paddle member, and
   a serpentine cam slot in one of said paddle members and a cam follower pin in the other of said members,
   said cam follower pin being engaged in said cam slot to translate linear motions of said actuator into a plurality of different types of motions of said first dilator paddle.

2. The speculum according to claim 1 further comprising
   a pawl attached to said actuator, and
   a ratchet bar means in said handle,
   said pawl being engaged with said ratchet bar to permit opening movement of said dilator paddles, but to lock against closing movement of said dilator paddles.

3. The speculum according to claim 2 further comprising
   a spring for holding said pawl in engagement with said ratchet bar, whereby, when said spring is sufficiently flexed said pawl disengages from said ratchet bar to permit said closing movement of said dilator paddles.

4. The speculum according to claim 3 wherein said pawl is a double sided pawl, and said ratchet bar means comprises
   a pair of oppositely disposed ratchet bars, one on each side of said double-sided pawl whereby each side of said double-sided pawl engages one of said ratchet bars.

5. The speculum according to claim 1 wherein said pivot member comprises
   a plastic living hinge.

6. The speculum according to claim 1 further comprising
   an undercut in said inner surface of at least one of said dilator paddles to leave a gap between said paddles when said dilator paddles are fully closed.

7. The speculum according to claim 1 further comprising
   a fluid reservoir built into the inner surface of said second dilator paddle.

8. A speculum for dilating an internal body cavity for examination, said speculum comprising
two paddle members for dilating said body cavity,
a handle member attached to one of said paddle members and including a ratcheting mechanism, a retention slot and a cam slot, and
a thumb pad attached by a hinging mechanism to the other one of said paddle members and including a pawl, a retention pin and a cam follower pin,
said pawl being engaged with said ratcheting mechanism, said retention pin being engaged in said retention slot and said cam follower pin being engaged in said cam slot when said two paddle members are assembled together,
said cam slot including at least two linear portions at an angle with respect to each other so as to cause said paddle members to initially move linearly with respect to each other and thereafter to move rotationally at said hinging mechanism with respect to each other.

9. The speculum according to claim 8 further comprising
means for spring-loading said pawl against said ratcheting mechanism.

10. The speculum according to claim 9 wherein said hinging mechanism comprises a plastic living hinge.

11. The speculum according to claim 8 wherein the leading edges of at least one of said paddle members are undercut to leave an opening at the pivot end of said at least one paddle member when said paddle members are closed together.

* * * * *